(12) United States Patent
Alshehri et al.

(10) Patent No.: US 12,048,420 B1
(45) Date of Patent: Jul. 30, 2024

(54) DENTAL CLAMP RETRACTOR

(71) Applicant: KING SAUD UNIVERSITY, Riyadh (SA)

(72) Inventors: Abdulaziz Mohammed Yahya Alshehri, Riyadh (SA); Majed Abdulaziz Alatrouzi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/639,513

(22) Filed: Apr. 18, 2024

(51) Int. Cl.
*A61B 1/24* (2006.01)
*A61B 1/32* (2006.01)
*A61C 19/00* (2006.01)

(52) U.S. Cl.
CPC ............ *A61B 1/24* (2013.01); *A61B 1/32* (2013.01); *A61C 19/001* (2013.01)

(58) Field of Classification Search
CPC .. A61B 1/24; A61B 1/32; A61B 13/00; A61C 5/90; A61C 19/001
See application file for complete search history.

(56) References Cited

U.S. PATENT DOCUMENTS

| 2,600,001 | A |  | 6/1952 | Kanter |  |
|---|---|---|---|---|---|
| 5,503,556 | A |  | 4/1996 | Leonard et al. |  |
| 5,800,173 | A |  | 9/1998 | Heasley |  |
| 5,803,734 | A | * | 9/1998 | Knutson | .......... A61C 5/82 433/136 |
| D491,663 | S |  | 6/2004 | Bat-Genstein |  |
| 9,610,009 | B2 | * | 4/2017 | Motamedi | ........... A61C 5/90 |
| 10,314,672 | B2 |  | 6/2019 | Alzain |  |
| 2006/0063979 | A1 |  | 3/2006 | Rosenblood et al. |  |
| 2020/0275991 | A1 |  | 9/2020 | Abedi et al. |  |

FOREIGN PATENT DOCUMENTS

| CN | 211674882 U | 10/2020 |
|---|---|---|
| FR | 2502931 A1 | 10/1982 |
| JP | 2000185057 A | 7/2000 |

* cited by examiner

*Primary Examiner* — Larry E Waggle, Jr.
(74) *Attorney, Agent, or Firm* — Nath, Goldberg & Meyer; Joshua B. Goldberg

(57) ABSTRACT

A dental clamp retractor includes tongue and cheek retractor portions separated by a clamp bow having an arcuate shape. A buccal extension arm extends laterally outward from the clamp bow to the cheek retractor portion. A buccal gauze holder is connected to the clamp bow by a flexible arm. The tongue retractor portion connects to the clamp bow by a lingual extension arm. A lingual gauze holder is connected to the clamp bow by a flexible arm. The cheek retractor portion may have a larger surface area than the tongue retractor portion and be formed of an elastomer. The buccal gauze holder and lingual gauze holder may be formed by clips. A dental procedure includes applying the dental clamp retractor to a patient to retract the tongue and cheek and hold gauze on a buccal and/or labial side of a tooth surface of the patient.

15 Claims, 2 Drawing Sheets

DENTAL CLAMP RETRACTOR

BACKGROUND

Field

The disclosure of the present patent application relates to dental retractors, and particularly to a dental retractor for the tongue and cheek capable of holding gauze on the buccal and lingual surfaces.

Description of Related Art

Dental procedures, in particular those involving posterior molars and wisdom teeth, often require the use of dental retractors and gauze. Molars and wisdom teeth are located deep within the mouth, making them challenging to access and visualize properly. Dental retractors help to hold back the cheeks, lips, and tongue, providing better visibility and access to the treatment area for the dentist or dental assistant.

Gauze is often used to absorb saliva and moisture from the oral cavity during dental procedures. Excessive moisture can interfere with the bonding of dental materials, such as fillings or crowns, and affect the overall success of the procedure. By keeping the treatment area dry, gauze helps to ensure optimal conditions for dental bonding and other dental treatments.

Dental retractors and gauze help to protect soft tissues, such as the cheeks, lips, and tongue, from accidental injury during dental procedures. By holding back these tissues and providing a clear working space, dental retractors minimize the risk of trauma or damage to surrounding oral structures.

Prior art devices exist but often serve a singular purpose, either retraction or application of gauze. A need exists for a singular device capable of holding gauze on either a buccal or lingual surface, while also performing retraction of the tongue and cheek.

SUMMARY

A dental clamp retractor is disclosed herein including tongue and cheek retractor portions. A clamp bow is included having an arcuate shape for extension over the occlusal tooth surface of a patient. A buccal extension arm extends laterally outward from the clamp bow and connects the clamp bow to the cheek retractor portion. A buccal gauze holder is included, as is a buccal flexible arm connected to the buccal gauze holder. The buccal flexible arm extends from an intersection point between the buccal extension arm and the clamp bow.

A lingual extension arm extends laterally outward from the clamp bow and connects the clamp bow and the tongue retractor portion. A lingual gauze holder is included, and a lingual flexible arm connected to the lingual gauze holder. The lingual flexible arm extends from an intersection point between the lingual extension arm and the clamp bow. The buccal extension arm may be longer than the lingual extension arm. The cheek retractor portion may have a larger surface area than the tongue retractor portion. The dental clamp retractor may be prefabricated and formed from a flexible metal or a flexible polymer material, and the cheek retractor portion may be formed from an elastomer material. The buccal gauze holder and the lingual gauze holder may be formed by clips. The clips may include an upper arm and a lower arm, the upper arm and lower arm joined by a connecting arch.

Further disclosed is a dental procedure which includes applying the dental clamp retractor set forth herein to a patient. The dental clamp retractor is used to retract the cheek and tongue of the patient and hold gauze on a buccal and/or labial side of a tooth surface of the patient. The dental clamp retractor may be manufactured as disposable or single use. The retractor may be pre-manufactured to specific size dimensions according to different groups of patients, such as children and adults and/or small, medium and large sizes, etc.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1A:
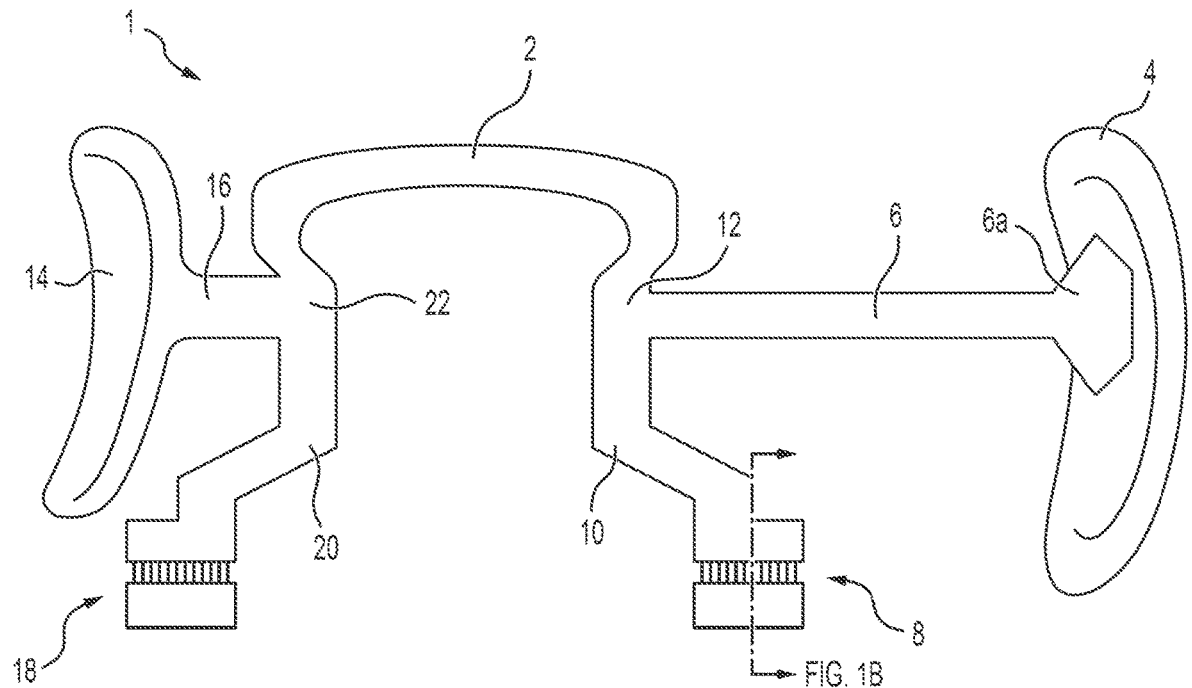
FIG. 1A is a rear view of a dental clamp retractor.

A dental clamp retractor 1 is disclosed herein. The dental clamp retractor 1 includes a clamp bow 2 having an arcuate shape for extension over the occlusal tooth surface of a patient. A buccal extension arm 6 is included extending laterally outward from the clamp bow 2 in connection to cheek retractor portion 4. Cheek retractor portion 4 may be formed from an elastomeric material such as rubber or silicone to provide a soft, cushioned surface for the inner cheek, while the dental clamp retractor 1 may be formed from a flexible metal or a flexible polymer. Distal end 6a of buccal extension arm 6 may be joined to cheek retractor portion 4 by any suitable means, such as adhesive bonding, mechanical fastening, over-molding, heat sealing, bonding, insert molding, etc. A buccal flexible arm 10 extends from an intersection point 12 between buccal extension arm 6 and clamp bow 2. Buccal flexible arm 10 is connected to a buccal gauze holder 8.

Further included is a tongue retractor portion 14 and a lingual extension arm 16. In some embodiments, the cheek retractor portion 4 may have a larger surface area than the tongue retractor portion 14 due to the larger size needed for retraction of a cheek in comparison to that of a tongue, whereby in some cases a smaller tongue retraction portion may prove more comfortable to the patient while still effectively retracting the tongue. The sizes of all elements of the retractor may be customized to various dimensions to fit different sized mouths, such as smaller sizes for children and various larger sizes available for adults.

Figure 1B:
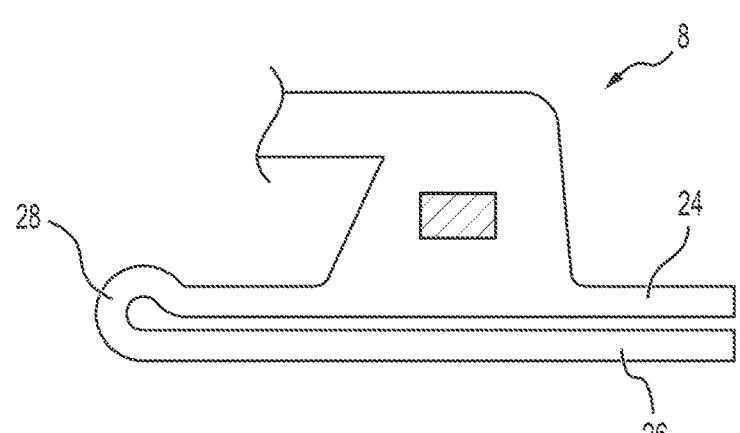
FIG. 1B is a right side view of a clip of a dental clamp retractor.

The lingual extension arm 16 extends laterally outward from the clamp bow 2 in a direction opposite to the extension of the buccal extension arm 6 and connects the clamp bow 2 to the tongue retractor portion 14. In other words, lingual extension arm 16 and buccal extension arm 6 are on opposite sides of the clamp bow 2 as shown in the figures. A lingual flexible arm 20 extends from an intersection 22 between clamp bow 2 and lingual extension arm 16. Lingual flexible arm 20 extends to a lingual gauze holder 18. In a non-limiting example, buccal gauze holder 8 and lingual gauze holder 18 each may be formed by clips, as shown in FIGS. 1A, 1B. The clips may include upper arm 24 and lower arm 26 joined by a connecting arch 28.

Figure 2A:
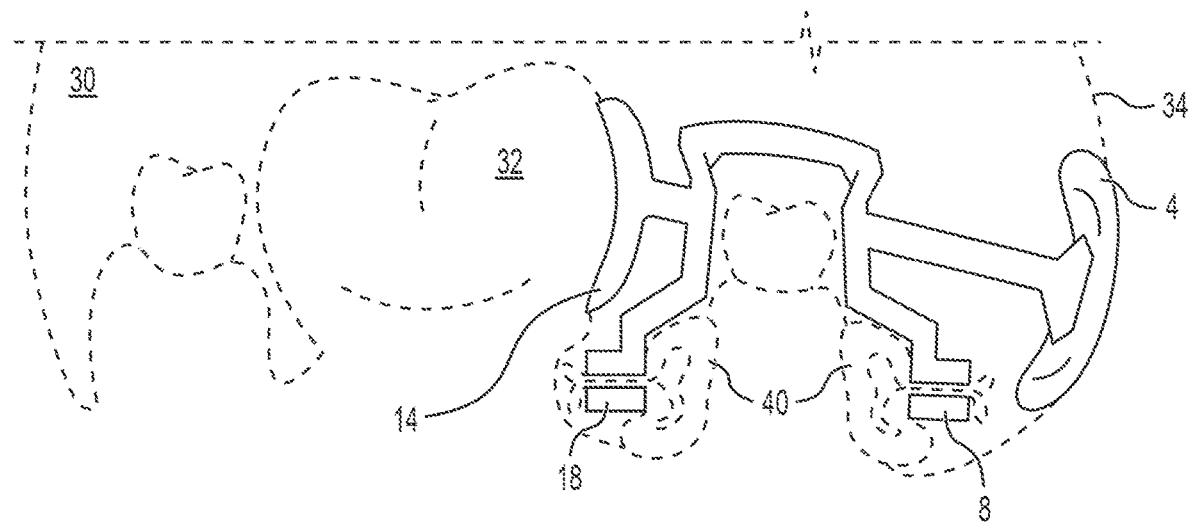
FIG. 2A is an environmental rear view of a dental clamp retractor applied to a patient's mouth.
Figure 2B:
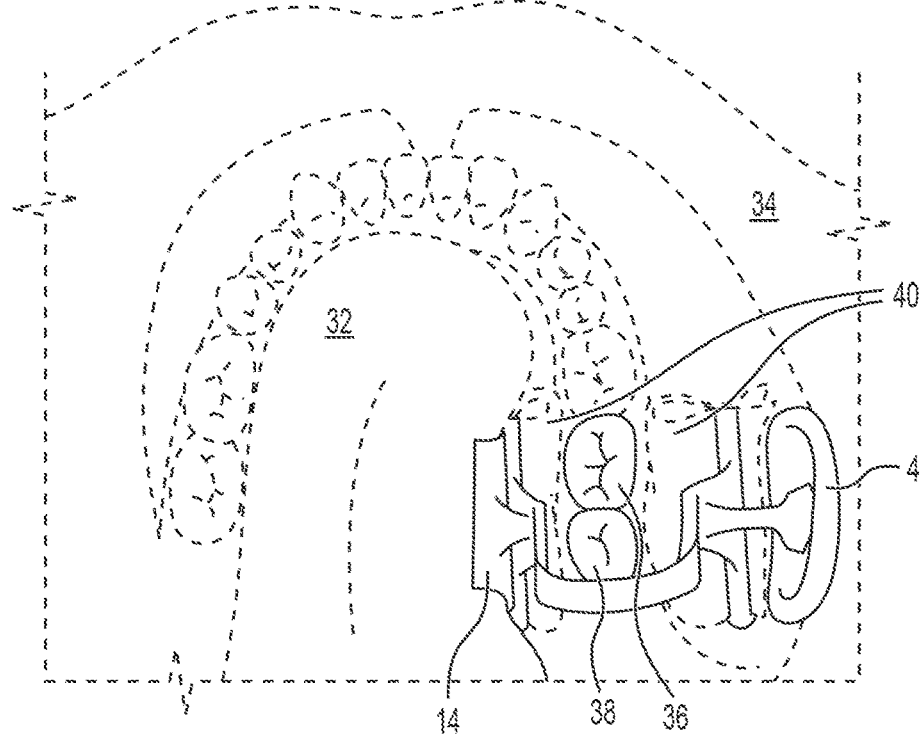
FIG. 2B is an environmental top view of a dental clamp retractor applied to a patient's mouth.

Turning to FIGS. 2A and 2B, the dental clamp retractor 1 is shown applied to a patient's mouth 30 in the posterior mouth region surrounding a wisdom tooth 38 and second molar 36. Tongue retractor portion 14 engages tongue 32 and keeps tongue 32 away from the teeth of interest 38, 36. Likewise, cheek retractor portion 4 retracts cheek 34 laterally outward and away from teeth 38, 36. Example procedures in which the retractor might be used include, but are not limited to, dental fillings, root canals, crowns, bridges, implants, extractions, and orthodontic treatments. Dental clamp retractor 1 may be manufactured inexpensively to be disposable after a single usage.

Individual pieces of gauze 40 are shown held by both buccal clip 8 and lingual clip 18 to keep the procedural site dry. The use of gauze aids in moisture control during a dental procedure to absorb fluids such as saliva and blood from the mouth. This is particularly important during procedures such as fillings or cementation of restorations, where moisture can interfere with the bonding process or affect the quality of the dental materials being used. Furthermore, the use of the gauze 40 to absorb fluids may help with patient comfort to prevent a gagging reflex as well as the dentist's visibility by absorbing fluids which might otherwise obstruct the field of view.

It is to be understood that the dental clamp retractor is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A dental clamp retractor comprising:
    a clamp bow having an arcuate shape for extension over an occlusal tooth surface of a patient;
    a cheek retractor portion;
    a buccal extension arm, wherein the buccal extension arm extends laterally outward from the clamp bow and connects the clamp bow to the cheek retractor portion;
    a buccal gauze holder;
    a buccal flexible arm connected to the buccal gauze holder, the buccal flexible arm extending from an intersection point between the buccal extension arm and the clamp bow;
    a tongue retractor portion;
    a lingual extension arm, wherein the lingual extension arm extends laterally outward from the clamp bow in a direction opposite to the buccal extension arm and connects the clamp bow and the tongue retractor portion;
    a lingual gauze holder; and
    a lingual flexible arm connected to the lingual gauze holder, the lingual flexible arm extending from an intersection point between the lingual extension arm and the clamp bow.

2. The dental clamp retractor as recited in claim 1, wherein the buccal gauze holder and the lingual gauze holder each are clips.

3. The dental clamp retractor as recited in claim 2, wherein the clips each have an upper arm and a lower arm joined by a connecting arch.

4. The dental clamp retractor as recited in claim 1, wherein the cheek retractor portion has a larger surface area than the tongue retractor portion.

5. The dental clamp retractor as recited in claim 1, wherein the buccal extension arm is longer than the lingual extension arm.

6. The dental clamp retractor as recited in claim 1, wherein the dental clamp retractor is formed of a flexible polymer material.

7. The dental clamp retractor as recited in claim 1, wherein the dental clamp retractor is formed of flexible metal.

8. The dental clamp retractor as recited in claim 1, wherein the cheek retractor portion is formed of an elastomer material.

9. The dental clamp retractor as recited in claim 1, wherein the dental clamp retractor is manufactured for single usage.

10. A dental procedure which includes applying the dental clamp retractor of claim 1 to a patient.

11. The dental procedure as recited in claim 10, wherein the dental clamp retractor is pre-manufactured to specific size dimensions according to the patient.

12. The dental procedure as recited in claim 10, further comprising using the dental clamp retractor to retract a cheek and tongue of the patient.

13. The dental procedure as recited in claim 12, further comprising using the dental clamp retractor to hold gauze on a buccal side of a tooth surface of the patient.

14. The dental procedure as recited in claim 12, further comprising using the dental clamp retractor to hold gauze on a labial side of a tooth surface of the patient.

15. The dental procedure as recited in claim 12, further comprising using the dental clamp retractor to hold gauze on both a buccal and a labial side of a tooth surface of the patient.

* * * * *